US006551794B1

(12) United States Patent
Burton et al.

(10) Patent No.: US 6,551,794 B1
(45) Date of Patent: *Apr. 22, 2003

(54) STABLE BIOTINYLATED BIOMOLECULE COMPOSITION

(75) Inventors: Steven James Burton, Peterborough (GB); James C. Pearson, Cambridge (GB); Peter A. D. Edwardson, Chester (GB); Alan Menzies, Connah's Quay (GB)

(73) Assignee: E. R. Squibb & Sons, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/555,602

(22) Filed: Nov. 9, 1995

(51) Int. Cl.[7] ......................... A61K 5/00; C07K 17/00; C12N 11/02; G01N 33/53
(52) U.S. Cl. ..................... 435/68.1; 424/1.69; 435/7.5; 435/13; 435/111; 435/174; 435/177; 514/2; 530/381; 530/382; 548/303.7
(58) Field of Search ................ 435/68.1, 966, 435/967, 972, 7.5, 13, 111, 174, 177; 548/303.7; 530/501–387; 514/2; 424/1.69

(56) References Cited

U.S. PATENT DOCUMENTS

| 3,779,706 A | * 12/1973 | Nabb ........................ 21/54 R |
| 4,709,037 A | 11/1987 | Sigler |
| 4,775,636 A | 10/1988 | Moeremans et al. |
| 4,794,082 A | 12/1988 | Sigler |
| 4,798,795 A | 1/1989 | Sigler |
| 4,806,343 A | * 2/1989 | Carpenter et al. .......... 424/450 |
| 4,897,364 A | 1/1990 | Gawronski .................. 435/14 |
| 5,026,785 A | 6/1991 | Mage et al. |
| 5,043,288 A | 8/1991 | Motsenbocker |
| 5,168,049 A | 12/1992 | Meade et al. |
| 5,306,824 A | 4/1994 | Powers et al. |
| 5,691,152 A | * 11/1997 | Burton et al. ................ 435/7.5 |
| 5,942,406 A | * 8/1999 | Burton et al. ................ 435/7.5 |
| 5,998,155 A | * 12/1999 | Burton et al. ................ 435/7.5 |
| 6,022,951 A | * 2/2000 | Sano et al. .................. 530/350 |
| 6,046,024 A | * 4/2000 | Burton et al. ............... 435/68.1 |
| 6,262,236 B1 | * 7/2001 | Edwardson et al. ........ 530/382 |

FOREIGN PATENT DOCUMENTS

| DE | 3629194 | 3/1987 |
| EP | 0365449 | 4/1990 |
| EP | 0592242 | 8/1993 |
| EP | 0726310 A | 8/1996 |
| JP | 63246382 | 2/1987 |
| JP | 458155 | 6/1990 |
| WO | WO 95 15371 A | 6/1995 |

OTHER PUBLICATIONS

Hasty et al, "Effects of Fibronectin . . . Cells", 1987, Infect. Immun 55 (9)., pp. 2103–2109, see abstract.*
Stults et al. "Use of Recomb. Biotinyl. Aequorin . . . ", Biochem., 31, pp. 1433–442, 1992.*
Muzykantov, V.R. et al, Analytical Biochemistry, vol. 226, No. 2, pp. 279–287, Apr. 10,1995.
Patent Abstract of Jaan, vol. 1995, No. 11, Dec. 26, 1995, & JP 07 194378A (Fuji Seito KK), Aug. 1, 1995.
Hollingsbee, D.A. et al, Thrombosis and Haemostasis, vol. 73, No. 6, Jun. 1995, p. 1470, Abstract.
Burton, S.J. et al, Thrombosis and Haemostasis, vol. 73, No. 6, Jun. 1995, p. 1469, Abstract.
Bayer and Wilchek, *Journal of Chromatography*, "Application of avidin–biotin technology to affinity–based separations," 510 (1990) pp. 3–11.

* cited by examiner

*Primary Examiner*—David M. Naff
*Assistant Examiner*—Deborah K. Ware
(74) *Attorney, Agent, or Firm*—John M. Kilcoyne

(57) ABSTRACT

Stable compositions containing biotinylated molecules, such as enzymes, are provided. The compositions include a biotinylated biomolecule, a biomolecule protectant, a buffer, a bulking agent selected from one or more water soluble, nonionic polymers and preferably a terminal sterilization protectant. The compositions can be utilized either as aqueous solutions or preferably in dried form, e.g., as a lyophilized, powder cake. They have applicability in any case where avidin/biotin technology is used and are particularly important as compositions containing a thrombin-like enzyme, e.g., for preparation of a fibrin monomer and fibrin monomer-based fibrin sealants.

25 Claims, No Drawings

STABLE BIOTINYLATED BIOMOLECULE COMPOSITION

BACKGROUND

The avidin-biotin affinity-based technology has found wide applicability in numerous fields of biology and biotechnology since the pioneering work by Dr. Edward Bayer and Dr. Meier Wilchek in the 1970's. The affinity constant between avidin and biotin is remarkably high and is not significantly lessened when biotin in coupled to a wide variety of biomolecules. Further, this affinity is substantially maintained even when cerivatized forms of the biotin are employed and numerous chemistries have been identified for coupling biomolecules to biotin with minimal or negligible loss in the activity or other desired characteristics of the biomolecule. In certain applications, avidin is immobilized onto an inert material over which a solution containing biotinylated biomolecules is passed. The affinity of the biotin for the avidin provides for the separation of the biomolecule from the solution. A review of the biotin-avidin technology can be found in Applications of Avidin-Biotin Technology to Affinity-Based Separation, Bayer, et al., *J. of Chromatography*, 1990, pgs. 3–11.

EP 592242 describes a novel fibrin sealant based on fibrin monomer as opposed to the traditional fibrinogen-based sealants andinvolves subjecting fibrinogen to a thrombin-like enzyme which is preferably removed after such treatment. EP 592242 describes that the enzyme captureand removal can be accomplished by using biotinylated batroxobin which can be recaptured with an avidin material. This and other applications would benefit by more convenient forms of biotinylated biomolecule and avidin materials. Presently, these materials are sometimes difficult to work with, can be unstable, can lose enzyme activity in processing such as lyophilization, may be unduly hygroscopic and do not withstand sterilization processes.

SUMMARY OF THE INVENTION

In accordance with the present invention, novel compositions and methods for biotinylated biomolecules and the biotin/avidin affinity technology are described. The novel composition involving biotin comprises:

i) a biotinylated biomolecule;
ii) a biomolecule protectant;
iii) buffer means to maintain a desired pH; and
iv) one or more bulking agents selected from water soluble, nonionic polymers.

This composition is conveniently an aqueous solution and preferably includes an agent to protect the composition against instability during terminal sterilization. Most preferably, this composition is freeze-dried to provide a stable, irradiatable powder form of the biotinylated biomolecule. Methods for making a fibrin monomer material, useful, for example, in a fibrin sealant, are also disclosed.

DETAILED DESCRIPTION OF THE PREFERRED EMBODIMENTS

The present invention discloses novel, stable compositions of biotin-biomolecule. The preferred compositions are freeze-dried and are stable, easy to handle, and can be terminally sterilized, e.g., by gamma irradiation without damage to the compositions. This is especially advantageous when the composition is a biotinylated biomolecule because it has been found to be very efficient to be able to terminally sterilize the lyophilized biotinylated biomolecule without damage to its activity. The present lyophilized biotin-based compositions have wide applicability wherever the avidin-biotin technology is useful because these compositions are water soluble, have low moisture uptake, have low bioburden, can be terminally sterilized (e.g., irradiated), remain stable and are pharmacologically acceptable. These advantages are provided by the unique combination of protectants and bulking agents as described herein.

These novel compositions include, along with the biotinylated biomolecule, a biomolecule protectant, buffer means to maintain the desired pH and one or more water soluble, nonionic polymer bulking agents. Preferably, the composition further includes an agent to protect the composition against deleterious effects of terminal sterilization, e.g., gamma irradiation. The biomolecule can be any desired enzyme or protein which is to be used in a biotinylated form. Numerous biotinylated biomolecules exist in the prior art and all of those prior biomolecules are useful herein as well. With regard to the novel fibrin monomer process in the above-referenced EP 592242, thrombin-like enzymes are useful in a biotinylated form. Such thrombin-like enzymes include thrombin or a thrombin-like enzyme selected from Acutin, Venzyme, Ancrod, Asperase, Batroxobin (from B. Altrox, B. Moojeni or B. Maranhao), Botropase, Crotolase, Flavoxogin and Gabonase. Nonlimiting examples of other biotinylated biomolecules include biotinylated lectins, antibodies, mitogens, DNA, RNA, tRNA, rRNA fragments, nucleosomes, membranes, membrane proteins, glycoproteins and synthetic peptides.

The biotin component of the biotinylated biomolecule can be biotin or any derivatized form or analog thereof, or any molecule having an affinity for avidin including monomeric avidin, Strept avidin, or any protein having biotin-binding properties including recombinant forms of any of the above. Patents and literature are replete with the various biotin compounds including various spacers, linking groups and the like, for use in the present applications. Nonlimiting examples can be found in M. D. Savage, et al. (1992), Pierce Chemical Co., *Avidin-Biotin Chemistry: A Handbook*; DE 3629194, U.S. Pat. Nos. 5,180,828, 4,709,037 and 5,252, 743, 4,798,795, 4,794,082, WO 85/05638 incorporated herein by reference.

The biomolecule protectant of the novel biotin compositions is any agent capable of protecting the desired activity of the biomolecule and thereby imparting stability to the biomolecule composition. Biomolecule protectants include, but are not limited to, trehalose, glycerol, ammonium sulphate and amino acids. Preferably the biomolecule protectant is an amino acid and, more preferably, the amino acid is a simple zwitterion such as glycine, alanine and valine with glycine being most preferred.

The buffer means of the present biotin compositions can be any convenient buffer suitable for maintaining the pH of the composition at a desired level. In the fibrin monomer process of EP 592242 it is desired to maintain the biotinylated biomolecule at about pH7, therefore sodium barbital, citrate, sodium barbital phosphate, potassium phosphate, imidazole-HCI, piperazine, sodium bicarbonate-5% $CO_2$, triethano amine-HCI—NaOH, tris (hydroxymethyl) aminomethane and sodium phosphate bufferare useful with sodium phosphate being preferred.

The bulking agent of the present biotin-biomolecule compositions is selected from water soluble, nonionic polymers. The bulking agent provides both chemical and physical stability to the present compositions and, for example, it presents the novel compositions when in the form of a freeze-dried cake from collapsing. The nonionic water soluble polymers also provide protection to the biomolecule. Dextran and similar polysaccharides have been found to enhance the stability of the present compositions. Nonlimiting examples of such bulking agents include dextran, polyvinylpyrrolidone, polyvinylalcohol, polyethyleneglycol, hydrolyzed starch and polysaccharides (e.g., lactose, glucose, maltose, mannitol, etc.) with dextran, especially dextrans having a molecular weight between 50,000 and 100,000 Daltons (e.g., Dextran T-70 from Pharmacia Co.) being preferred.

The optional terminal sterilization protectant is selected from antioxidants, free radical scavengers and reducing agents. Preferred are antioxidants such as reduced glutathione, α-tocopherol, N,N-dimethyl-p-phenylenediamine and sodium ascorbate with sodium ascorbate being most preferred.

Preparation of the biotinylated molecule is accomplished by known techniques. For example, a biotin derivative (which can be any desired biotin compound with spacer arm and/or leaving groups as discussed above) such as N-hydroxysuccinimide-biotin (NHS-biotin) can be reacted with the desired biomolecule, e.g., the soluble enzyme Batroxobin, in a solvent and in the presence of a buffer. The NHS functions as a leaving group to provide the so-formed biotin Batroxobin. This can be purified using standard methodology, for example, subjecting the biotin Batroxobin to purification on a Sephadex™ chromatography column to remove free biotin, NHS-biotin and other low molecular weight solutes.

Thereafter, an aqueous solution is prepared comprising the components of the composition, i.e., the biotinylated biomolecule, biomolecule protectant, buffer means and bulking agent. Preferably, the purification step above can utilize the buffer desired to be in the end product, which provides that water and bulking agent are added to the biotinylated biomolecule and buffer to form the aqueous solution.

The aqueous solution of this invention comprises:

0.01 to 50% by weight of biomolecule protectant;

1 to 50% by weight of bulking agent;

the biotinylated biomolecule in a concentration selected according to the particular application;

water; and buffer necessary to maintain the desired pH.

This solution or suspension is also a useful, stable form of the biotinylated biomolecule and, as such, is considered a part of the present invention. If sterility is required, the solution can be prepared aseptically or can include the optional terminal sterilization protectant if terminal sterilization, e.g., gamma irradiation, is to be employed. The terminal sterilization protectant is typically present in the aqueous solution in an amount of from about 0.01% to about 10%.

These ranges are especially useful for compositions. containing from 0.1 to about 1.0 mg of enzyme or biomolecule per ml of composition and will also provide significant protection for compositions containing up to 5 mg of enzyme per ml of composition. Preferably, for compositions containing more than 1 mg/ml of enzyme and especially for compositions containing more than 5 mg/ml, the percentages of each component should be increased in a manner roughly proportional to the increase in enzyme concentration.

A preferred aqueous composition of the present invention comprises about 2% of biomolecule protectant, about 2% bulking agent, about 50 mM buffer, about 0.25% terminal sterilization protectant and the required concentration (preferably 0.1–0.5 mg/ml) of biomolecule.

Most preferred is when the biomolecule is Batroxobin in an amount of from about 50 to 200 activity units per milliliter of solution, and when the composition includes 2% by weight glycine, 50 millimolar sodium phosphate buffer (to maintain pH7), 2% by weight dextran and 0.25% by weight sodium ascorbate.

In a preferred embodiment of the present invention, the aqueous solution is lyophilized to provide a convenient powder composition typically in the, form of a cake. Lyphophilization techniques are well known and any suitable technique can be employed. One suitable lyophilization, i.e., freeze drying process involves pre-cooling the lyophilization apparatus to −45° C., freezing the solution to −40° C., warming the product to −25° C. and holding for 11 hours or more, cooling the product to −43° C., introducing a reduced pressure (i.e., vacuum) to about 0.1 millibar and maintaining reduced pressure at −43° C. until drying is complete as is evidenced by cessation of water vapor evolution, reducing the pressure to the lowest setting while raising the temperature in 5° C./hour increments to 30° C. and holding the so-treated product at 30° C. for at least 5 hours.

The compositions of this invention involving a biotinylated form of thrombin or a thrombin-like enzyme, e.g., Batroxobin, are useful to convert fibrinogen, or a fibrinogen-containing composition, into fibrin monomer, or a fibrin monomer-containing composition. Accordingly, the present invention further includes a novel method, to prepare a fibrin monomer useful, for example, in preparing a fibrin sealant. This novel method involves subjecting a source of fibrinogen to a stable, biotinylated thrombin or thrombin-like enzyme composition as defined herein to convert fibrinogen into fibrin monomer, "capturing" the biotinylated enzyme with an avidin material, and removing the enzyme which is a part of the so-formed biotin/avidin complex.

Although in an ideal setting some of the avidin should "leach" from its agarose (or other inert) support and hopefully all of the biotinylated biomolecule is captured by the avidin/inert support material, it is understood that this may not always be the case. It has now been found that free avidin, leached from its inert support, is capable of coupling with a biotinylated biomolecule (e.g., baxtroxobin) or vice versa, affording capture and removal of the enzyme complex from solution. Accordingly, the reliability of the present compositions and methods are further enhanced by the self-scavenging medonium described herein.

The compositions of the present invention can further be incorporated into a processing unit, e.g., an automated centrifuge for preparing fibrin monomer as defined above. The biotinylated biomolecule composition can be preloaded into the processing unit in powder form or can be lyophilized in situ in the device or in a controlled release compartment of the device.

The biotinylation of the biomolecule can be accomplished, as discussed above, by any known biotinylation process. It has been found that careful control of the ratio of biotins to biomolecules is important in the ultimate desired performance of the biomolecule. For example, regarding biotinylated batroxobin for use in the process of preparing a fibrin monomer in EP 592242, it is important for the batroxobin to maintain sufficient activity so as to efficiently convert the fibrinogen to fibrin monomer. It is also important for the biotinylated batroxobin to be readily captured by the avidin material for thorough separation of the enzyme from the fibrin-monomer product. In the case of batroxobin, in theory, 14 biotin molecules can be coupled to the enzyme. In accordance with the present invention, it has been found that the mean number of biotin molecules per Batroxobin molecules in a composition should be in the range 5–12 and preferably 6–8. It is believed that if the mean is below about 5, that a significant number of Batroxobin molecules may actually not be biotinylated, resulting in incomplete enzyme capture. It has also been found that if the mean is above about 8, the batroxobin activity is reduced. This is believed to have applicability to other biomolecules as well, especially to the thrombin and thrombin-like enzymes. Accordingly, compositions containing biomolecules having 10 or more binding sites per biomolecule capable of reacting with a biqtinylation reagent should have a mean number of at least 5 and preferably 6 biotins/biomolecule. It should be understood by those skilled in the art that these preferred ranges of biotins per biomolecule can be reduced if any surface reaction sites on the biomolecule are hyperactive or if the biotinylation process involves physical protection of part of the biomolecule surface (from biotinylating agents), e.g., by reversibly binding the biomolecule to a solid surface.

The biotinylated biomolecule compositions of the present invention are stable compositions which can withstand lyophilization, terminal sterilization while maintaining a remarkable amount of biomolecule integrity and excellent uptake by avidin molecules. This invention will be further described by the Examples below, however, it should not be limited by the details described therein.

EXAMPLE 1

To a solution of batroxobin (10.75 mg; 3560 units) in 0.2 M sodium bicarbonate buffer, pH 8.5 (1.6 ml) was added water (1.6 ml) followed by 0.08 ml of a solution comprising N-hydroxysuccinimido biotin (13.5 mg) in DMSO (1 ml). The mixture was stirred for 1 hour at 20° C. then applied directly to a column (1 cm dia.×40 cm) of Sephadex G-25 chromatography media previously equilibrated in a solution comprising 10 mM sodium phosphate buffer, pH 7.0 and glycine (1% w/v). The biotin-batroxobin was eluted from the column at a flow rate of 0.4 ml/min. The first UV absorbing peak to be eluted from the column containedpurified biotin batroxobin which was determined to be free of any remaining biotinylation reagent and associated degradation products. These were present in the second UV absorbing peak to be eluted from the column. The purified biotin-batroxobin contained 6.9 moles of biotin per mole of batroxobin. When the purified biotinylated batroxobin was mixed for 5 minutes at 20° C. with a suspension of avidin agarose gel in 0.2 M sodium acetate buffer, pH 4.0, >99.5% of the purified biotinylated batroxobin was captured.

EXAMPLE 2

Purified biotin-batroxobin prepared as described in Example 1 was diluted with a solution comprising 10 mM sodium phosphate buffer, pH 7.0 and glycine (1% w/v) to provide a solution of biotin-batroxobin containing 235 batroxobin activity units per milliliter. One volume of this solution was mixed with 1 volume of a solution comprising: glycine (3% w/v), dextran (4% w/v), ascorbic acid (0.5% w/v) and sodium dihydrogen orthophosphate (90 mM) adjusted to pH 7.0 by addition of sodium hydroxide. Biotin-batroxobin formulated in this manner was found to exhibit no loss of enzyme activity when stored for 1 month at −20° C., 4° C. and 20° C.

EXAMPLE 3

Formulated biotin-batroxobin prepared as described in Example 2 was filled intoglass vials (0.3 ml per vial) and placed in a lyophilization apparatus. The formulated biotin-batroxobin was cooled to −40° C. then warmed to −25° C. and held at this temperature for 11 hours. At the end of this period, the formulated biotin batroxobin was cooled to −43° C. and the pressure reduced to 0.1 millibars. These conditions were maintained throughout the primary drying phase which was complete after 22 hours. On completion of primary drying, the pressure was reduced to 0.08 millibars and the freeze dried biotin batroxobin warmed to 30° C. at an incremental increase of 5° C. per hour. The freeze dried biotin-batroxobin was held at 30° C. for 5 hours prior to removal from the lyophilization apparatus.

Examination of the freeze dried biotin batroxobin showed no loss of batroxobin activity occurred during the freeze drying process. Freeze dried formulations of biotin-batroxobin prepared in this manner exhibited no loss of batroxobin activity after storage at 4° C. for 3 months. When the freeze dried biotin-batroxobin was reconstituted with water and mixed for 5 minutes at 20° C. with a suspension of avidin agarose gel in 0.2M sodium acetate buffer; pH 4.0, >99.5% of the biotinylated batroxobin was captured.

EXAMPLE 4

Freeze dried biotin-batroxobin prepared as described in Example 3 was subjected to a sterilizing dose (25 kilo grays) of gamma radiation. Following an initial loss of batroxobin activity constituting 10–15% of the initial activity present, no further loss of batroxobin activity was observed over a 1 month period. No degradation of the irradiated biotin-batroxobin was apparent following electrophoretic analysis by polyacrylamide gel electrophoresis. When the gamma irradiated freeze dried biotin-batroxobin was reconstituted with water and mixed for 5 minutes at 20° C. with a suspension of avidin agarose gel in 0.2M sodium acetate buffer, pH 4.0, >99.5% of the biotinylated batroxobin was captured.

Table 1 gives further examples of formulated biotin-batroxobin compositions which may be prepared by the methods of Example 1 and Example 2 except the column equilibration buffer in Example 1 and the formulation buffers in Example 2 are adjusted to provide the corresponding amount of dextran, glycine and ascorbic acid in the final formulated biotin-batroxobin solution as stated in columns II, III and IV of Table 1. These formulated solutions of biotin-batroxobin were freeze dried according to the method of Example 3 and subjected to gamma irradiation according to the method of Example 4. The percentage batroxobin activity remaining after gamma irradiation is given in column V of Table 1. The example number of this invention is given in column I of Table 1.

TABLE I

| I | II Dextran (% w/v) | III Glycine (% w/v) | IV Ascorbic acid (% w/v) | V Batroxobin activity remaining (%) |
|---|---|---|---|---|
| 5 | 2 | 0 | 0 | 40 |
| 6 | 0 | 2 | 0 | 59 |
| 7 | 2 | 2 | 0 | 61 |
| 8 | 2 | 2 | 0.2 | 92 |
| 9 | 5 | 5 | 0.25 | 99 |

What is claimed is:

1. A stable composition containing a biotinylated biomolecule comprising:
   said biotinylated biomolecule;
   a biomolecule protectant selected from the group consisting of an amino acid, trehalose, glycerol and ammonium sulphate;
   buffer means to maintain pH of said stable composition at a predetermined value; and one or more water soluble bulking agents;
   and further wherein said amino acid is a single zwitterion selected from the group consisting of glycine, alanine and valine.

2. The composition of claim 1 further comprising a terminal sterilization protectant to protect said composition and biotinylated biomolecule from degradation or instability during terminal sterilization, said terminal sterilization protectant selected from the group consisting of antioxidants, free radical scavengers and reducing agents.

3. The composition of claim 2 wherein said antioxidants are selected from the group consisting of reduced glutathione, α-tocopherol, N,N-dimethyl-p-phenylenediamine and sodium ascorbate.

4. A method for the terminal sterilization of a biotinylated biomolecule which provides sterility for said biotinylated biomolecule while maintaining stability and biomolecule activity which method comprises subjecting a composition of claim 2 to terminal sterilization conditions to provide for said terminal sterilization of the biotinylated biomolecule.

5. The method of claim 4 wherein said biotinylated biomolecule is in a dry powder form.

6. The composition of claim 1 wherein said biotinylated biomolecule is selected from enzymes coupled to biotin or an analog or derivatized form of biotin; and/or proteins coupled to biotin or an analog or derivatized form of biotin.

7. The composition of claim 6 wherein said enzymes are thrombin or a thrombin-like enzyme selected from the group consisting of Acutin, Venzyme, Ancrod, Asperase, Batroxobin, Botropase, Crotolase, Flavoxogin and Gabonase.

8. The composition of claim 7 wherein the biotinylated biomolecule is biotin-Batroxobin.

9. The composition of claim 1 wherein said buffer means maintains the pH of said composition at about 7.

10. The composition of claim 9 wherein said buffer means is selected from the group consisting of sodium phosphate, sodium barbital, citrate, sodium barbital phosphate, potassium phosphate, imidazole-HCl, piperazine, sodium bicarbonate-5% $CO_2$, triethanolamine-HCl—NaOH, tris(hydroxymethyl)aminomethane and sodium phosphate buffer.

11. The composition of claim 1 wherein the bulking agents are selected from nonioic water soluble polymers.

12. The composition of claim 11 wherein said polymers are selected from the group consisting of polyvinylpyrrolidone, polyvinylalcohol, polyethyleneglycol and polysaccharides.

13. The composition of claim 12 wherein said polysaccharides are selected from the group consisting of dextran, hydrolyzed starch, lactose, glucose, maltose and mannitol.

14. The composition of claim 13 wherein said dextran has a molecular weight between about 50,000 and 100,000 Daltons.

15. The composition of claim 1 wherein said composition is an aqueous solution.

16. The composition of claim 15 wherein said biotinylated biomolecule is present in an amount of from about 50 to about 200 activity units per ml of said solution.

17. The composition of claim 16 wherein said biotinylated biomolecule is present in an amount of from about 100 to about 135 activity units per ml of said solution.

18. The composition of claim 15 further comprising between about 0.01 and about 10.0 percent by weight of a terminal sterilization protectant.

19. The composition of claim 18 wherein said terminal sterilization protectant is present in an amount of about 0.25 weight percent.

20. The composition of claim 1 or 2 in the form of a dry powder.

21. In a method for subjecting a sample to a biotinylated biomolecule wherein the improvement comprises introducing, as the biotinylated biomolecule, a stable composition of claim 1.

22. In a method for producing a fibrin monomer comprising subjecting a fibrinogen-containing composition to a biotinylated enzyme to convert said fibrinogen to fibrin monomer such that a mixture of fibrin monomer and biotinylated enzyme is formed;
   introducing a material having an affinity for biotin into the mixture of fibrin monomer and biotinylated enzyme so that a complex of said material and said biotinylated enzyme are formed;
   separating the complex, and thereby said enzyme, from the fibrin monomer;
   wherein the improvement comprises introducing, as the biotinylated enzyme, a stable composition of claim 1.

23. In a method employing biotin-avidin affinity to form a complex of a biotinylated comprising subjecting a biotinylated biomolecule to avidin for the purpose of coupling of the biotinylated biomolecule and forming a complex of the biotinylated biomolecule with the avidin, wherein the improvement comprises introducing, as the biotinylated biomolecule, a stable composition of claim 1.

24. A stable composition containing a biotinylated biomolecule comprising:
   said biotinylated biomolecule;
   a biomolecule protectant selected from the group consisting of an amino acid, trehalose, glycerol and ammonium sulphate;
   buffer means to maintain pH of said stable composition at a predetermined value;
   one or more water soluble bulking agents; and
   a terminal sterilization protectant selected from the group consisting of antioxidants, free radical scavengers and reducing agents; further wherein said antioxidants are selected from the group consisting of glutathione, α-tocopherol, N,N-dimethyl-p-phenylenediamine and sodium ascorbate.

25. A stable composition containing a biotinylated biomolecule comprising:
   said biotinylated biomolecule;
   a biomolecule protectant selected from the group consisting of an amino acid, trehalose, glycerol and ammonium sulphate;
   buffer means to maintain pH of said stable composition at a predetermined value;
   one or more water soluble bulking agents;
   wherein said composition is an aqueous solution and wherein said biotinylated biomolecule is present in an amount from about 50 to about 200 activity units per milliliter of said solution.

* * * * *